United States Patent [19]

Matsunaga et al.

[11] 4,154,967

[45] May 15, 1979

[54] PROCESS FOR PREPARATION OF PHENOLS

[75] Inventors: Fujihisa Matsunaga, Iwakuni; Hirohiko Nambu, Ohtake, both of Japan

[73] Assignee: Mitsui Petrochemical Industries, Ltd., Tokyo, Japan

[21] Appl. No.: 794,654

[22] Filed: May 6, 1977

[30] Foreign Application Priority Data

May 7, 1976 [JP] Japan .................................. 51-51308
May 7, 1976 [JP] Japan .................................. 51-51309

[51] Int. Cl.$^2$ ..................... C07C 39/04; C07C 37/00; C07C 39/08
[52] U.S. Cl. ..................................... 568/771; 568/800
[58] Field of Search ........... 260/621 G, 621 C, 610 R, 260/610 B, 604, 624; 568/771, 800

[56] References Cited

U.S. PATENT DOCUMENTS 2,662,923  12/1953  Reeder .............................. 260/621 G

FOREIGN PATENT DOCUMENTS 1222070  8/1966  Fed. Rep. of Germany ...... 260/621 G
1164962  9/1969  United Kingdom ................ 260/610 B

*Primary Examiner*—James O. Thomas, Jr.
*Assistant Examiner*—Werren B. Lone
*Attorney, Agent, or Firm*—Wenderoth, Lind & Ponack

[57] ABSTRACT

A process for producing phenols which comprises oxidizing an aromatic hydrocarbon ring-substituted by an isopropyl group in one step in the liquid phase using molecular oxygen or a gas containing molecular oxygen in the presence or absence of a solvent, wherein the oxidation is carried out in the presence of an aromatic mercaptan having an acid dissociation constant (pKa) of less than 7.8.

10 Claims, No Drawings

PROCESS FOR PREPARATION OF PHENOLS

This invention relates to an improved process for preparing phenols such as phenol, cresol or hydroquinone, which comprises the one-step liquid-phase oxidation of the corresponding aromatic hydrocarbons ring-substituted by an isopropyl group, such as cumene, cymene or diisopropyl benzene, with molecular oxygen or molecular oxygen-containing gas in the presence or absence of a solvent. More specifically, the process is characterized in that the one-step liquid-phase oxidation is carried out in the presence of an aromatic mercaptan having an acid dissociation constant (pKa) of less than 7.8, and if desired, in the additional presence of an organic carboxylic acid.

Conventional production of phenols such as phenol or cresol relies on a two-step liquid-phase oxidation process which comprises oxidizing an aromatic hydrocarbon ring-substituted by an isopropyl group in the liquid phase with molecular oxygen or a molecular oxygen-containing gas in the presence or absence of a solvent, and usually in the presence of a radical initiator, to form the corresponding hydroperoxide, and cleaving the product with a strong acid such as sulfuric acid, as schematically shown below by an example of forming cresol from cymene.

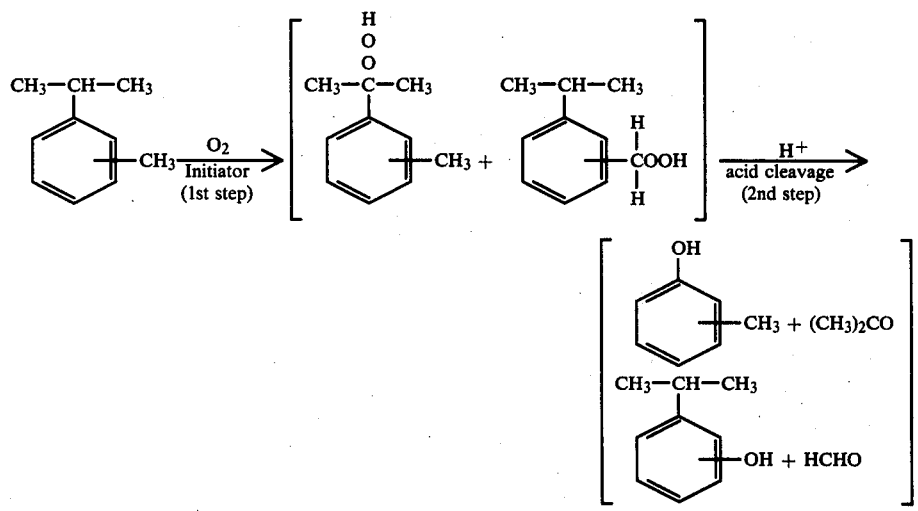

In the actual operation of the conventional process, the first step of liquid-phase oxidation with air is carried out in the presence of an alkali such as sodium carbonate in order to neutralize the by-product carboxylic acid and allow the reaction to proceed smoothly. The resulting cymene hydroperoxide is concentrated, and then the second step of acid cleavage of the cymene hydroperoxide is performed. It is further necessary to recover cresol from the acid cleavage product by fractional distillation. The process therefore requires four steps in total.

In an attempt to overcome the disadvantage of the multi-step process, it was suggested to produce phenols by a one-step liquid-phase oxidation process without going through the acid cleavage step. For example, Japanese Laid-Open Patent Publication No. 34840/73 (laid open on May 22, 1973) discloses a process for producing phenol by the one-step liquid-phase oxidation of cumene with a molecular oxygen-containing gas in the presence of one type of halogen and/or hydrogen halide and in the presence or absence of a solvent, preferably in the co-presence of a radical initiator. Japanese Laid-Open Patent Publication No. 54010/73 (laid open on July 30, 1973; published on Aug. 6, 1976 as Japanese Patent Publication No. 26427/76) discloses a process for producing cresol by the one-step liquid-phase oxidation of cymene in the presence of a hydrogen halide similarly to the first-mentioned process. Furthermore, Industrial & Engineering Chemistry, Vol. 41, No. 11, November 1949, pages 2612 to 2616 states in the introductory part at page 2612 that hydrogen bromide is also a catalyst for the oxidation of alkylbenzenes in liquid phase, although this publication deals mainly with the gas-phase oxidation of hydrocarbons catalyzed by hydrogen bromide.

Production of phenols by the one-step liquid-phase oxidation process using a molecular oxygen-containing gas in the presence of halogen or hydrogen halide described above suffers from various defects. For example, the halogen or hydrogen halide dissipates out of the system from the top of the oxidation apparatus as entrained by the unreacted molecular oxygen-containing gas, and is difficult to recover. The halogen or hydrogen halide also heavily corrodes the oxidation apparatus and distillation apparatus. Such a gas is consumed by reaction with the aromatic hydrocarbon as a reactant or with phenols or ketones as products to form a large quantity of by-product tar. Furthermore, being gaseous, the halogen or hydrogen halide is difficult to handle in its transportation and its recovery from the reaction product, and the amount of the halogen or hydrogen halide used naturally increases.

The present inventors worked extensively on commercially feasible one-step liquid-phase oxidation processes, and found that in the one-step liquid-phase oxidation of an aromatic hydrocarbon ring-substituted by an isopropyl group with molecular oxygen or a molecular oxygen-containing gas in the presence or absence of a solvent, if necessary in the co-presence of a radical initiator, the addition of a small amount of an aromatic mercaptan having an acid dissociation constant (pKa) of less than 7.8, preferably less than 6.3, to the oxidation reaction system can lead to the elimination of the aforesaid defects. Being liquid or solid, the aromatic mercaptan is not carried away from the reaction system by the unreacted molecular oxygen-containing gas, and is very easy to handle in transportation or recovery from the reaction product. Moreover, it does not corrode the reaction apparatus. An additional advantage is that since the aromatic mercaptan has poor reactivity with the aromatic hydrocarbons as reactants or phenols or ketones as products, its loss by consumption is small, and the amount of tar formed as a by-product decreases. Accordingly, the use of the specified aromatic mercaptans has successfully overcome the disadvantages associated with the conventional multi-step and one-step processes described above.

It has also been found that an organic carboxylic acid can be used together with the aromatic mercaptan, and aromatic mercaptans having a relatively large acid dissociation constant (pKa) can conveniently be used.

It is an object of this invention to provide a commercial process for producing phenols by the one-step liquid-phase oxidation of aromatic hydrocarbons ring-substituted by an isopropyl group.

The above and other objects of this invention and its advantages will become more apparent from the following description.

The process of the present invention can be operated in the same way as in the conventional liquid-phase oxidation methods except the oxidation is carried out in the presence of an aromatic mercaptan or in the additional presence of an organic carboxylic acid, and no additional operation or equipment is required in particular. The aromatic mercaptan can be added to the reaction system by any desired means. Usually, the aromatic mercaptan is mixed with the starting aromatic hydrocarbon, and the mixture is fed into the reaction system. The organic carboxylic acid can be fed into the reaction system in a similar manner. If desired, the aromatic mercaptan or the inorganic acid may be fed separately from the starting aromatic hydrocarbon.

The reaction sufficiently proceeds at room temperature, and heating is not required in particular. However, for promoting the oxidation reaction the reaction is preferably carried out under heating conditions. Usually, the reaction temperature is from 20° to 150° C. The reaction can be performed under atmospheric pressure or under elevated pressures, for example 1 to 50 atmospheres, preferably 5 to 10 atmospheres.

The reaction is performed in the presence of molecular oxygen, or a molecular oxygen-containing gas, such as air or an oxygen gas diluted with an inert carrier gas such as nitrogen or argon. For example, in the presence of molecular oxygen or a molecular oxygen-containing gas, the starting aromatic hydrocarbon is stirred or shaken in the presence of the aromatic mercaptan to contact the starting material with the molecular oxygen sufficiently. Or molecular oxygen or a molecular oxygen-containing gas is blown into the starting aromatic hydrocarbon in the presence of the aromatic mercaptan thereby to contact the starting material with molecular oxygen. Or both of these expedients may be employed together.

The reaction may be carried out in the presence of a radical initiator such as azobisisobutyronitrile, benzoyl peroxide, t-butyl peroxybenzoate, acetyl peroxide and lauroyl peroxide. The suitable amount of the initiator is at least about 0.05% by weight, preferably 0.5 to 5% by weight, based on the starting aromatic hydrocarbon.

According to the process of the present invention, the reaction can be carried out smoothly without using an alkali such as sodium carbonate as in the two-step oxidation processes heretofore known. The reaction can be carried out either batchwise or continuously, but the continuous method is preferred. It is especially preferable that the oxidation be carried out at a reaction temperature of 50° to 90° C. with a residence time of 0.5 to 5 hours until the conversion of the aromatic hydrocarbon reaches 30 to 60%. This permits the continuous performance of stable oxidation. The reaction product consists mainly of acetone, organic carboxylic acid, the unreacted aromatic hydrocarbon, phenol, aromatic mercaptan, and a disulfide obtained by partial oxidation of the aromatic mercaptan. After separating acetone by distillation from the product, the organic carboxylic acid and unreacted aromatic hydrocarbon are separated by distillation and recycled to the oxidation reaction system for re-use. The phenol is then separated by distillation, and the residue is sent to a reducing step where the disulfide is reduced with hydrogen using molybdenum sulfide, cobalt sulfide or nickel sulfide as a catalyst, thereby to convert the disulfide to the aromatic mercaptan. The aromatic mercaptan is then purified by distillation, and recycled to the oxidation reaction system for re-use.

The starting aromatic hydrocarbon used in the process of the present invention is an aromatic hydrocarbon which contains an isopropyl group substituted at the aromatic ring. The aromatic ring is, for example, a benzene ring or a naphthalene ring. Preferred aromatic hydrocarbons are compounds of the following formula

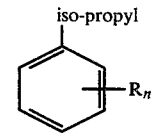

wherein R represents a lower alkyl group, for example of 1 to 3 carbon atoms, and n is 0 or and integer of 1 or 2. Examples of the starting aromatic hydrocarbon are cumene, cymene, β-isopropyl naphthalene, diisopropyl benzene, triisopropyl benzene, 3,5-dimethylisopropyl benzene, and mixtures of these. The mixture may isomeric an isometric mixture, for example a mixture of meta-cymene and para-cymene, or a mixture of homologs, for example a mixture of cumene and cymene. From the starting aromatic hydrocarbons, the corresponding phenols can be produced, for example, phenol from cumene, cresol from cymene, β-naphthol from β-isopropyl naphthalene, and hydroquinone from p-diisopropyl benzene.

The one-step liquid-phase oxidation in the process of this invention is carried out in the presence of an aromatic mercaptan having an acid dissociation constant (pKa) of less than 7.8, preferably less than 6.3. Specific examples of the aromatic mercaptan are shown below (the numbers in the parentheses show pKa values).

Aromatic mercaptans in which the mercapto group is directly substituted at the aromatic ring, such as meta-iodophenyl mercaptan (6.8), para-iodophenyl mercaptan (6.9), meta-chlorophenyl mercaptan (6.7), para-chlorophenyl mercaptan (7.0), meta-fluorophenyl mercaptan (6.8), para-fluorophenyl mercaptan (7.5), meta-bromophenyl mercaptan (6.8), para-bromophenyl mercaptan (7.0), meta-acetyl phenyl mercaptan (6.9), para-acetyl phenyl mercaptan (5.9), meta-nitrophenyl mercaptan (5.9), para-nitrophenyl mercaptan (5.0), meta-cyanophenyl mercaptan (6.3), para-cyanophenyl mercaptan (6.0), meta-methylsulfonylphenyl mercaptan (5.9), para-methylsulfonylphenyl mercaptan (5.6), metamercaptobenzenesulfonic acid (5.9), para-mercaptobenzenesulfonic acid (5.7), orthocarboxyphenyl mercaptan (5.6), para-carboxyphenyl mercaptan (5.9), 2,4-dinitrophenyl mercaptan (4.0), 2,4,6-trinitrophenyl mercaptan (3.2), 3,4-dichlorophenyl mercaptan (6.2), 3,5-dichlorophenyl mercaptan (5.8), 2-chloro-5-trifluoromethylphenyl mercaptan (6.0), 3-trifluoromethyl-4-chlorophenyl mercaptan (6.2), 2,4,5-trichlorophenyl mercaptan (4.2), pentachlorophenyl mercaptan (3.5), and pentafluorophenyl mercaptan (2.7); and aromatic mercaptans having a mercapto-containing functional group such as thiobenzoic acid (6.3).

The aromatic mercaptans having a mercapto group directly substituted at the aromatic ring are preferred. Especially preferred species are phenyl mercaptans containing 1 to 3 substituents selected from the class consisting of cyano, acetyl, nitro, halogen, halo-lower alkyl, lower alkylsulfonyl and sulfonic acid groups.

The pKa value is determined by the following method.

Three samples of each aromatic mercaptan are weighed into 50 ml, volumetric flasks which have previously been swept out with nitrogen. To minimize atmospheric oxidation, this nitrogen atmosphere is maintained while each flask is promptly processed, one at a time, according to the following procedure. Twenty-five milliliters of 96% ethanol at 25° C. is added from a pipet, and the flask again is swept out with nitrogen before agitating to dissolve the sample. Sufficient standard carbonate-free sodium hydroxide solution is then measured from a buret into the flask to partially neutralize the aromatic mercaptan (about 20, 40 or 60% in turn). The solution is then made up to the mark with carbonate-free water, and again swept with nitrogen before inverting to mix. An aliquot is then withdrawn and added to an excess of standard iodine solution. While this is allowed to stand for a few minutes, another sample is withdrawn and the pH measured immediately with a Beckman Model G pH meter. The iodine solution is then titrated with thiosulfate so that the exact —SH content of the solution can be calculated. The pKa is then computed using the Henderson equation, $pKa - pH + \log (ArSH/ArS^-)$. The value from the iodine titration is used for the stoichiometric concentration of aromatic mercaptan, and the concentration of anion is taken as equal to that of the sodium hydroxide added. The concentration of un-ionized aromatic mercaptan can then be obtained by difference. The compounds are measured at concentrations of 0.01 to 0.05 M depending on their solubility.

The aromatic mercaptan can be used in an amount of usually 0.1 to 2 moles, preferably 0.1 to 1 mole, per mole of the aromatic hydrocarbon.

The organic carboxylic acid that may be present in the reaction system in addition to the aromatic mercaptan includes aliphatic carboxylic acids, for example, $C_2$–$C_5$ aliphatic carboxylic acids and their halogenated products. Examples of preferred aliphatic carboxylic acids are acetic acid, propionic acid and butyric acid, and preferred halogenated aliphatic carboxylic acids include monochloroacetic acid, dichloroacetic acid, trichloroacetic acid, difluoroacetic acid, and trifluoroacetic acid. The amount of the organic carboxylic acid is not limited in particular since it can also be utilized as a solvent. For example, the organic carboxylic acid can be used in an amount of 0.1 mole to about 5 moles, preferably about 0.2 to about 1 mole, per mole of the starting aromatic hydrocarbon.

Usually, the one-step liquid-phase oxidation in accordance with the present invention is carried out in the absence of a solvent, but may be carried out in the presence of an additional solvent. Examples of the additional solvent are hydrocarbons such as benzene, toluene, xylene, hexane, heptane, and cyclohexane, and halogenated hydrocarbons such as chlorobenzene, bromobenzene and carbon tetrachloride.

The following examples illustrate the present invention in greater detail.

EXAMPLE 1 AND COMPARATIVE EXAMPLE 1

A 100 ml. flask was charged with 8.1 millimoles of para-cymene, 0.07 millimole of azobisisobutyronitrile and 1.0 millimole of para-nitrophenyl mercaptan having a pKa of 5.0, and shaken in an atmosphere of oxygen at 60° C. for 20 hours. The amount of oxygen absorbed was 0.38 millimole, and para-cresol was formed in an amount of 0.27 millimole, at a selectivity of 90.4%.

When the above procedure was repeated without adding para-nitrophenyl mercaptan, the amount of oxygen absorbed was 0.63 millimole, and para-cresol was not formed at all but a great amount of cymene hydroperoxide was formed.

EXAMPLES 2 AND 3 AND COMPARATIVE EXAMPLE 2

A 100 ml. flask was charged with para-cymene and azobisisobutyronitrile in the amounts indicated in Table 1 and each of the mercaptans shown in Table 1 in the amounts indicated, and shaken in an atmosphere of oxygen at 60° C. for 20 hours.

The amount of oxygen absorbed and the yielded amount and selectivity of para-cresol are shown in Table 1.

Table 1

| Example (Ex) or Comparative Example (CE.) | para-Cymene (millimoles) | Azobisisobutyronitrile (millimoles) | Mercaptan (millimoles) | Amount of oxygen absorbed (millimoles) | para-Cresol Yielded amount (millimoles) | Selectivity (%) |
|---|---|---|---|---|---|---|
| Ex. 2 | 8.3 | 0.07 | para-Acetylphenyl mercaptan (pKa = 5.9) 1.1 | 0.42 | 0.31 | 91.2 |
| Ex. 3 | 8.5 | 0.06 | para-Methylsulfonylphenyl mercaptan (pKa = 5.6) 1.2 | 0.45 | 0.29 | 92.1 |
| CE. 2* | 8.54 | 0.08 | Phenylmer- | 0.23 | 0 | 0 |

Table 1-continued

| Example (Ex) or Comparative Example (CE.) | para-Cymene (millimoles) | Azobisisobutyronitrile (millimoles) | Mercaptan (millimoles) | Amount of oxygen absorbed (millimoles) | para-Cresol Yielded amount (millimoles) | Selectivity (%) |
|---|---|---|---|---|---|---|
| | | | captan (pKa = 7.8) 1.58 | | | |

*A large quantity of dimethyltolyl carbinol was formed.

COMPARATIVE EXAMPLE 3

A 300 ml flask was charged with 6.35 millimoles of para-cymene, 0.5 millimole of azobisisobutyronitrile and 2 millimoles of hydrogen bromide, and shaken in an atmosphere of oxygen at 70° C. for 5 hours. The conversion of para-cymene was 16%; the yield of para-cresol was 9%; and the selectivity of para-cresol was 58%.

EXAMPLES 4 AND 5

A 100 ml flask was charged with para-cymene and para-nitrophenylmercaptan in the amounts shown in Table 2 and each of the initiators shown in Table 2 in the amounts indicated, and then shaken in an atmosphere of oxygen at each of the temperatures indicated in Table 2 for 5 hours.

The amount of oxygen absorbed and the yielded amount and selectivity of para-cresol are shown in Table 2.

EXAMPLES 6 AND 7

A 100 ml flask was charged with cumene or paradiisopropylbenzene, azobisisobutyronitrile and para-nitrophenyl mercaptan in the amounts indicated in Table 3, and then shaken in an atmosphere of oxygen at 60° C. for 20 hours. The amount of oxygen absorbed, and the yielded amounts and selectivities of phenol, para-isopropylphenol and hydroquinone are shown in Table 3.

Table 3

| Example | Hydrocarbon (millimoles) | Azobisisobutyronitrile (millimoles) | para-Nitrophenyl mercaptan (millimoles) | Amount of oxygen absorbed (millimoles) | Phenols Yielded amount (millimoles) | Selectivity (%) |
|---|---|---|---|---|---|---|
| 6 | Cumene 8.1 | 0.06 | 1.0 | 0.41 | Phenol 0.29 | 92.0 |
| 7 | para-Diisopropyl benzene 8.0 | 0.06 | 1.1 | 0.45 | para-Isopropyl phenol 0.26 Hydroquinone 0.08 | 87.3 |

EXAMPLE 8 AND COMPARATIVE EXAMPLES 4 TO 6

A 100 ml flask was charged with para-cymene, azobisisobutyronitrile and trifluoroacetic acid in the amounts indicated in Table 4 and each of the mercaptans shown in Table 4 in the amounts indicated, and then shaken in an atmosphere of oxygen at 60° C. for 20 hours.

Table 2

| Example | Reaction temperature (°C.) | para-Cymene (millimoles) | Initiator (millimoles) | para-phenyl mercaptan (millimoles) | Amount of oxygen absorbed (millimoles) | para-Cresol Yielded amount (millimoles) | Selectivity (%) |
|---|---|---|---|---|---|---|---|
| 4 | 90 | 8.2 | Azobiscyclohexane carbonitrile 0.06 | 1.0 | 0.48 | 0.31 | 81.5 |
| 5 | 130 | 8.1 | t-Butyl hydroperoxide 0.04 | 1.1 | 0.83 | 0.45 | 70.3 |

The oxidation reaction product was analyzed, and the conversion of para-cymene, the yielded amount of para-cresol and the yield and selectivity of para-cresol were calculated. The results are shown in Table 4.

Table 4

| Example (Ex.) and Comparative Example (CE.) | para-Cymene (millimoles) | Azobisisobutyronitrile (millimoles) | Trifluoroacetic acid (millimoles) | Mercaptans (millimoles) | Amount of oxygen absorbed (millimoles) | Conversion of para-cymene (%) | para-Cresol Yielded amount (millimoles) | Yield (%) | Selectivity (%) |
|---|---|---|---|---|---|---|---|---|---|
| Ex. 8 | 6.38 | 0.06 | 1.02 | para-Nitrophenyl | 0.64 | 8.0 | 0.49 | 7.7 | 95.3 |

Table 4-continued

| Example (Ex.) and Comparative Example (CE.) | para-Cymene (milli-moles) | Azobis-isobutyro-nitrile (milli-moles) | Trifluoro-acetic acid (milli-moles) | Mercaptans (millimoles) | Amount of oxygen absorbed (milli-moles) | Conversion of para-cymene (%) | para-Cresol Yielded amount (milli-moles) | Yield (%) | Selec-tivity (%) |
|---|---|---|---|---|---|---|---|---|---|
| | | | | mercaptan (pKa = 5.0) 0.52 | | | | | |
| CE. 4* | 7.52 | 0.06 | None | None | 0.58 | 6.9 | 0 | 0 | 0 |
| CE. 5 | 11.86 | 0.10 | 1.87 | None | 0.17 | 1.5 | 0.036 | 0.3 | 19.9 |
| CE. 6 | 8.39 | 0.08 | 1.48 | Phenyl-mercaptan (pKa = 7.8) 1.59 | 0.48 | 4.6 | 0.33 | 4.0 | 86.9 |

*Cymene hydroperoxide was formed.

COMPARATIVE EXAMPLE 7

A 300 ml flask was charged with 3.15 millimoles of para-cymene, 0.5 millimole of azobiscyclohexyl carbonitrile and 1.1 millimoles of hydrogen bromide, and shaken in an atmosphere of oxygen at 90° C. for 5 hours.

The conversion of para-cymene was 14%; the yield of para-cresol was 9%; and the selectivity of para-cresol was 63%.

EXAMPLES 9 TO 12

A 500 ml flask was charged with para-cymene, azobisisobutyronitrile and para-nitrophenyl mercaptan (pKa=5.0) in the amounts shown in Table 5 and each of the organic carboxylic acids shown in Table 5 in the amounts indicated, and then shaken in an atmosphere of oxygen at 60° C. for each of the periods indicated in Table 5.

The oxidation reaction product was analyzed, and the conversion of para-cymene, the yielded amount, yield and selectivity of para-cresol were calculated. The results are shown in Table 5.

EXAMPLES 13 AND 14

A 500 ml flask was charged with para-cymene, acetic acid, para-nitrophenyl mercaptan and azobisisobutyronitrile in the amounts indicated in Table 6, and then shaken in an atmosphere of oxygen for 5 hours at each of the temperatures indicated in Table 6.

The oxidation reaction product was analyzed, and the conversion of para-cymene, and the yielded amount, yield and selectivity of para-cresol were calculated. The results are shown in Table 6.

Table 6

| Example | para-Cymene (milli-moles) | Azobis-isobutyro-nitrile (milli-moles) | para-Nitro-phenyl mercaptan (milli-moles) | Acetic acid (milli-moles) | Reaction temper-ature (°C.) | Amount of oxygen absorbed (milli-moles) | Conver-sion of para-cymene (%) | para-Cresol Yielded amount (milli-moles) | Yield (%) | Selec-tivity (%) |
|---|---|---|---|---|---|---|---|---|---|---|
| 13 | 27.7 | 0.5 | 8.0 | 74.7 | 50 | 14.5 | 73 | 15.0 | 54 | 75 |
| 14 | 27.8 | 0.5 | 8.0 | 75.4 | 60 | 22.5 | 80 | 17.1 | 62 | 77 |

EXAMPLES 15 TO 17

A 500 ml flask was charged with acetic acid and para-nitrothiophenol in the amounts indicated in Table 7, 0.5 millimole of azobisisobutyronitrile, and each of a mixture of meta-cymene and para-cymene, cumene, and para-diisopropylbenzene in the amounts indicated in Table 7, and then shaken in an atmosphere of oxygen at 60° C. for 25 hours.

The oxidation reaction product was analyzed, and the conversion of the hydrocarbon and the yielded amount, yield and selectivity of the phenol were calculated. The results are shown in Table 7.

Table 5

| Example | para-Cymene (milli-moles) | Azobis-isobutyro-nitrile (milli-moles) | para-Nitro-phenyl mercaptan (milli-moles) | Organic carboxylic acid (milli-moles) | Reaction time (hours) | Amount of oxygen absorbed (milli-moles) | Conver-sion of para-cymene (%) | para-Cresol Yielded amount (milli-moles) | Yield (%) | Selec-tivity (%) |
|---|---|---|---|---|---|---|---|---|---|---|
| 9 | 27.5 | 0.5 | 7.9 | Acetic acid 74.9 | 1.0 | 9.2 | 35 | 8.4 | 30 | 88 |
| 10 | 25.1 | 0.5 | 7.9 | Acetic acid 74.1 | 2.5 | 16.1 | 69 | 14.8 | 60 | 78 |
| 11 | 27.8 | 0.5 | 8.0 | Acetic acid 75.4 | 5.0 | 22.5 | 80 | 17.1 | 62 | 77 |
| 12 | 25.1 | 0.5 | 8.0 | Acetic acid 67.3 + Trichloro-acetic acid 10.0 | 5.0 | 21.5 | 81 | 14.6 | 58 | 71 |

Table 7

| Example | Hydrocarbon (millimoles) | para-Nitrophenyl mercaptan (millimoles) | Acetic acid (millimoles) | Amount of oxygen absorbed (millimoles) | Conversion of the hydrocarbon (%) | Phenols Yielded amount (millimoles) | Yield (%) | Selectivity (%) |
|---|---|---|---|---|---|---|---|---|
| 15 | Mixture of m- and p cymenes 28.3 | 8.0 | 77.5 | 13.5 | 44 | m- and p-cresol 10.4 | 37 | 84 |
| 16 | Cumene 31.6 | 8.0 | 77.2 | 14.7 | 47 | phenol 13.1 | 41 | 88 |
| 17 | para-Diisopropyl benzene 22.1 | 7.9 | 74.8 | 14.8 | 48 | p-Isopropyl phenol 6.5 Hydroquinone 2.3 | 50 | 95 |

EXAMPLES 18 TO 21

0.8 500 ml flask was charged with 28 millimoles of para-cymene, 75 millimoles of acetic acid and 0.8 mole of each of the aromatic mercaptans shown in Table 8, and shaken in an atmosphere of oxygen at 60° C. for 2.5 hours.

The oxidation reaction product was analyzed, and the conversion of para-cymene and the yield and selectivity of para-cresol were calculated. The results are shown in Table 8.

Table 8

| Example | Aromatic mercaptan | Conversion (%) | Yield (%) | Selectivity (%) |
|---|---|---|---|---|
| 18 | 3-Trifluoromethyl-phenyl mercaptan | 55 | 43 | 78 |
| 19 | 3-Trifluoromethyl-4-chlorophenyl mercaptan | 48 | 57 | 84 |
| 20 | 3,5-Dichlorophenyl mercaptan | 55 | 43 | 79 |
| 21 | 3,4-Dichlorophenyl mercaptan | 36 | 27 | 76 |

EXAMPLE 22

A 300 ml oxidation reaction tank was continuously charged with a solution consisting of 60% by weight of para-cymene, 25% by weight of acetic acid and 15% by weight of 3,4-dichlorophenyl mercaptan at a rate of 100 ml/hr (residence time : 3 hours), and the oxidation was continued until a steady state was reached, while blowing air into the solution. The oxidation reaction product was analyzed, and it was found that the conversion of p-cymene was 58 mole%, the yield of p-cresol was 54 mole%, and the selectivity of p-cresol was 93 mole%.

What we claim is:

1. A process for producing a phenol corresponding to an aromatic hydrocarbon of the formula

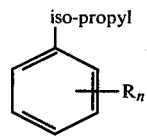

wherein R represents alkyl containing 1 to 3 carbon atoms of n is zero or an integer of 1 or 2, which comprises oxidizing said aromatic hydrocarbon in one step in a liquid phase with molecular oxygen or a gas containing molecular oxygen, at a temperature of 20° to 150° C. under a pressure from atmosphere pressure to 50 atmospheres, in the presence of a phenyl mercaptan containing 1 to 3 substituents selected from the group consisting of cyano, acetyl, nitro, halogen, halo-lower alkyl, lower alkylsulfonyl and sulfonic acid groups, said phenyl mercaptan having an acid dissociation constant of less than 7.8, with the proviso that when n is 1 and R is 4-isopropyl the phenol is hydroquinone.

2. The process of claim 1 wherein the oxidation is carried out in the additional presence of the organic carboxylic acid.

3. The process of claim 1 wherein the phenyl mercaptan has an acid dissociation constant of less than 6.3.

4. The process of claim 2 wherein the organic carboxylic acid is selected from the group consisting of aliphatic carboxylic acids containing 2 to 5 carbon atoms and their halogenated products.

5. The process of claim 1 wherein the oxidation is carried out in the additional presence of a radical initiator.

6. The process of claim 1 wherein the amount of the phenyl mercaptan is 0.1 to 2 moles per mole of the aromatic hydrocarbon.

7. The process of claim 1 wherein the oxidation is carried out at 50° to 90° C. with a residence time of 0.5 to 5 hours.

8. The process of claim 2 wherein the amount of the organic carboxylic acid is 0.1 to 5 moles per mole of the aromatic hydrocarbon.

9. The process of claim 5 wherein the amount of the radical initiator is at least about 0.05% by weight based on the weight of the aromatic hydrocarbon.

10. The process of claim 5 wherein the amount of the radical initiator is 0.5 to 5% by weight based on the weight of the aromatic hydrocarbon.

* * * * *